United States Patent [19]

Seib et al.

[11] 4,151,178

[45] Apr. 24, 1979

[54] METHOD OF SYNTHESIZING FATTY ACID ESTERS OF ASCORBIC ACID

[75] Inventors: Paul A. Seib, Manhattan, Kans.; Raymond C. Cousins, Washington, Mo.; Russell C. Hoseney, Manhattan, Kans.

[73] Assignee: Kansas State University Research Foundation, Manhattan, Kans.

[21] Appl. No.: 872,994

[22] Filed: Jan. 27, 1978

Related U.S. Application Data

[63] Continuation of Ser. No. 729,646, Oct. 5, 1976, abandoned.

[51] Int. Cl.$^2$ .......................................... C07D 307/62
[52] U.S. Cl. ................................................. 260/343.7
[58] Field of Search ..................................... 260/343.7

[56] References Cited

U.S. PATENT DOCUMENTS

| | | | |
|---|---|---|---|
| 2,350,435 | 6/1944 | Wells et al. | 260/343.7 |
| 2,408,897 | 10/1946 | Wells et al. | 260/343.7 |

FOREIGN PATENT DOCUMENTS

| | | | |
|---|---|---|---|
| 579333 | 7/1946 | United Kingdom | 260/343.7 |
| 585828 | 2/1947 | United Kingdom | 260/343.7 |
| 42-20051 | 10/1967 | Japan | 260/347.7 |

OTHER PUBLICATIONS

Delga et al., Ann. Pharm. France vol. 15, pp. 691–697 (1957).
Wertheim, Textbook of Organic Chemistry, 3rd Ed., frontispage, and pp. 231 to 233, The Blakiston Co. NY (1951).
Chemical Abstracts, vol. 68, abst. no. 96105r (1968), (brief abstract of Shionogi & Co., Japanese Pat. 20,051 supra).
Tanaka, Yakugaku Zasshi, vol. 86, pp. 376–383 (1966).

*Primary Examiner*—John D. Randolph
*Attorney, Agent, or Firm*—Schmidt, Johnson, Hovey & Williams

[57] ABSTRACT

A high-yield process of producing essentially pure fatty acid esters of ascorbic acid is disclosed which gives significantly increased yields of esters using a simple reaction scheme and an excess of relatively inexpensive, recoverable fatty acids, as opposed to use of an excess of ascorbic acid. The process hereof comprises reacting an ascorbic acid isomer and a saturated fatty acid in concentrated sulfuric acid at ambient or relatively low temperatures, followed by ester recovery. Surprisingly, enchanced yields are obtained by using a molar excess of fatty acid relative to the ascorbic acid, 98–99% concentrated sulfuric acid as opposed to 95% sulfuric acid, and/or a molar ratio of the sum of the fatty acid and ascorbic acid to sulfuric acid of from about 0.1 to 0.3.

8 Claims, No Drawings

METHOD OF SYNTHESIZING FATTY ACID ESTERS OF ASCORBIC ACID

This is a continuation of application Ser. No. 729,646, filed on Oct. 5, 1976, now abandoned.

This invention relates to a relatively inexpensive, high-yield process of synthesizing desirable fatty acid esters of ascorbic acid. More particularly, it is concerned with an improved process which achieves significantly enhanced yields of essentially pure product through careful control and maintenance of critical parameters such as relative ratios of reactants and the use of highly concentrated (i.e., above about 96%) sulfuric acid as the solvent. Operation in accordance with the present invention can give significant improvement in yeilds, as opposed to prior conventional methods. Such improved yields are especially critical when expensive reagents, such as L-ascorbic acid, are involved in chemical synthesis.

Fatty acid esters of ascorbic acid such as those made from palmitic, myristic and stearic acid have known utility as effective antioxidants in high fat foods such as nuts, potato chips, mayonnaise, margarines, and deep fat fried snack foods. In addition, salts of certain of these esters are useful as surfactants in food systems.

U.S. Pat. No. 2,350,435 describes the most common method of synthesizing 6-0-fatty acid esters of ascorbic acid. This method comprises dissolving a fatty acid in 95% sulfuric acid, along with an excess of ascorbic acid, whereupon the reaction mixture is allowed to stand overnight to form the desired 6-ester. Yields of recrystallized L-ascorbyl 6-laurate, 6-myristate, 6-palmitate and 6-stearate were reported to be on the order of 40–50%. However, since in all cases a 25% excess of L-ascorbic acid was used in the reactions, conversion of L-ascorbic acid to the appropriate esters was only on the order of 32–40%.

As noted, prior methods have without known exception employed an excess of ascorbic acid in the ester-forming reaction. This was done because of the fact that it was thought that ascorbic acid would degrade in concentrated sulfuric acid; accordingly, in order to provide sufficient ascorbic acid for the reaction, and to give a driving force thereto, excess ascorbic acid was used. The prediction that ascorbic acid wuold degrade by dehydration or polymerization in concentrated $H_2SO_4$ stems from the known fact that carbohydrates undergo dehydration reactions in hot dilute acid or in hot or cold concentrated sulfuric acid (see Feather et al., *Adv. in Carbohydrate Chem.*, 28 (1973), 161 and Scott et al., *Analytical Biochemistry*, 21 (1967), 68. It is also known that pentoses and L-ascorbic acid degrade totally in boiling dilute mineral acids to give 2-furaldehyde. Accordingly, since pentose sugars degrade in hot dilute acid or cold concentrated sulfuric acid, then predictably L-ascorbic acid (which degrades in hot dilute acid) should also dehydrate in concentrated sulfuric acid at room temperatures. Thus, in order to overcome this anticipated difficulty, excess ascorbic acid has been employed in making fatty acid esters of ascorbic acid.

The fact that prior investigators have employed an excess of ascorbic acid is undesirable for a member of reasons. First, ascorbic acid is normally much more expensive than the other main reactant, i.e., the fatty acid, and therefore to use the more expensive ascorbic acid in excess is economically unattractive. Moreover, excess ascorbic acid from the reaction cannot be recovered after completion of the reaction, and this further increases costs.

It is therefore the most important object of the present invention to provide an improved method of preparing 6-0-fatty acid esters of ascorbic acid which gives improved yield and allows use of an excess of fatty acids in the reaction mixture, as opposed to an excess of ascorbic acid, in order to lower reagent cost and permit recovery of any excess fatty acid.

As a corollary to the foregoing, another object of the invention is to provide a process of producing essentially pure fatty acid esters of ascorbic acid in which an ascorbic acid isomer and a molar excess of fatty acid are reacted in concentrated $H_2SO_4$ at ambient or relatively low temperatures; in the preferred method of the invention, highly concentrated $H_2SO_4$ (at least about 96%) is used as the solvent, and the mole ratio of the sum of the fatty acid and ascorbic acid to sulfuric acid is from about 0.1 to 0.3, as these conditions have been demonstrated as unexpectedly enhancing yield of the desired ester.

In its broadest aspects, the present invention is concerned with improved methods for giving high yields of 6-fatty acid esters of ascorbic acid. As discussed above, the basic known reaction involves reacting respective quantities of ascorbic acid and a selected fatty acid in concentrated $H_2SO_4$, whereupon the 6-ester can be recovered by conventional techniques. This basic method is disclosed in U.S. Pat. No. 2,350,435. In order to accomplish this objective of increased yields at lower cost, the invention hereof embraces several alternatives and aspects. For example, it has surprisingly been found that use of an excess of fatty acid is effective for this purpose, along with employment of highly concentrated $H_2SO_4$ and a specific mole ratio range of the sum of fatty acid and ascorbic acid to $H_2SO_4$. The unexpectedness of the improvements resulting from these method alterations is confirmed by virtue of the fact that no complete explanation has been found to explain why the desirable yield improvement occurs.

In more detail, it has first of all been discovered that, contrary to the expectations and predictions of those knowledgeable in the art, the isomers of ascorbic acid are very stable in concentrated $H_2SO_4$. For example, ultraviolet spectroscopy studies demonstrate that L-ascorbic acid ($3 \times 10^{-5}$M) in nitrogen-purged concentrated $H_2SO_4$ is not degraded at all over a period of 46 days. The significance of this finding is that it allows use of a molar excess of fatty acid in the esterification reaction mixture relative to the ascorbic acid (preferably the mole ratio of fatty acid to ascorbic acid ranges from about 1.1 to 1.5, and most preferably is about 1.35). Thus, the cheaper fatty acid component is used in excess to provide a driving force for the reaction without fear that degradation of the ascorbic acid will unacceptably limit yields. Moreover, this provides additional benefits since any excess fatty acid remaining after the esterification reaction is complete can be easily recovered from the final reaction products by known means.

It has also been found that the concentration of $H_2SO_4$ acid in the solvent medium is important to good yields. Broadly, the $H_2SO_4$ should have a concentration of at least about 96%, and preferably a concentration of from about 98 to 99%. Although the beneficial effect of using highly concentrated $H_2SO_4$ as opposed to the 95% $H_2SO_4$ heretofore employed is clear and unequivocally demonstrated hereinafter, the precise mechanism by which increased yields are accomplished through the use of highly concentrated $H_2SO_4$ is not understood.

Finally, it has also been discovered that the mole ratio of the sum of the fatty acid and ascorbic acid components to $H_2SO_4$ in the reaction mixture is important. This ratio should be within the range of from about 0.1 to 0.3, and most preferably on the order of from about 0.15 to 0.17. However, maintenance of the above ratio is most effective when the fatty acid is also present in molar excess relative to the ascorbic acid. The reason for these effects is likewise not fully understood.

In carrying out the reaction, the fatty acid should be saturated and have from 4 to 20 carbon atoms, inclusive, and more preferably from 12 to 18 carbon atoms, inclusive. Suitable fatty acids would include lauric, palmitic, myristic and stearic acids, for example. In the case of the ascorbic acid component, any of the isomers of ascorbic acid such as L-ascorbic or D-isoascorbic acid can be used to good effect.

The reaction can be carried out at relatively low temperatures, but higher temperatures can also be used under certain conditions without adversely affecting yields. A reaction temperature of from 20° to 50° C., and more preferably about 20°-25° C., has proven to be effective in practice. Also, it has been found that lower temperatures around 20° C. can be used with longer reaction times to give increased yields as compared with higher temperature, shorter reaction time methods. Similarly, although a reaction time of from 2 to 48 hours is broadly applicable, the preferred conditions of the invention achieve essentially complete ester formation within a period of from about 4 to 16 hours.

In the most preferred form of the invention all of the important factors mentioned above are optimized to give yields which in some cases represent 70% or more improvements over prior processes. In these cases the fatty acid is present in molar excess relative to the ascorbic acid, the $H_2SO_4$ is 98-99% concentrated, and the mole ratio of the sum of the fatty acid and ascorbic acid to $H_2SO_4$ is from about 0.1 to 0.3. This gives yields on the order of 75 to 85%, (in the case of L-ascorbyl 6-laurate and 6-palmitate) as compared to approximately 50% obtained with prior methods as represented by U.S. Pat. No. 2,350,435.

Recovery techniques used in the invention are essentially conventional. These may involve cooling and diluting the reaction mixture in ice after the esterification reaction is complete, followed by physical separation and ether extraction, brine washing of the ester extractions, and drying. These procedures (which may also include recrystallization) give good yields of chromatographically pure products. The recovered esters can also be converted to the corresponding salts using known means.

The following examples will illustrate the methods of the present invention and demonstrate the beneficial effects thereof in increasing yields. However, nothing in the examples is to be taken as a limitation on the invention.

EXAMPLE I

A series of esterification reactions were undertaken to determine the effect of varying (a) the concentration of $H_2SO_4$, (b) the amount of fatty acid used, (c) reaction times, (d) reaction temperature, and (e) the molar ratio of the sum of the fatty acid and ascorbic acid to $H_2SO_4$, in the preparation of L-ascorbyl-6-laurate.

In each reaction (unless otherwise specified) a quantity of L-ascorbic acid was added to 50ml of concentrated $H_2SO_4$ (either 95 or 99% $H_2SO_4$). A quantity of lauric acid was then added to the mixture with stirring until all of the lauric acid was dissolved, and thereafter for an additional specified reaction period and at a specified reaction temperature. The reaction mixture was poured onto 300 g of crushed ice with vigorous stirring and cooling at about 5° C. The cooled mixture was then transferred to a separatory funnel and extracted with 400 ml, and then 100 ml, of ether. The ether layers were combined and gently washed five times with 50-75 ml portions of half-saturated brine, dried over anhydrous sodium sulfate and filtered. The solvent was removed with a rotary vacuum evaporator with a warm (ca-55°) water bath, to give a pale-colored solid. This solid was washed three times with 100 ml portions of petroleum ether, with filtering after each wash, to give a solid product (dried at 25° under vacuum over anhydrous calcium sulfate). Recrystallization using 250-300 ml of ethyl ether plus 50 ml of petroleum ether gave analytically pure L-ascorbyl 6-laurate.

The percentage yield in each reaction was calculated from the weight of chromatographically pure, dry product produced, based upon the quantity of L-ascorbic acid initially used.

The results of this series of tests are set forth in Table I:

TABLE I

| Reaction | Sulfuric Acid Concentration | L-Ascorbic Acid, M | Molar Excess of Lauric Acid, % | Reaction Period, Hr. | Temp., °C. | Yield[1] |
| --- | --- | --- | --- | --- | --- | --- |
| 1[2] | 95% | 0.5 | −20 | 16 | 25 | 54[3] |
| 2 | 99% | 0.5 | −20 | 16 | 25 | 50 |
| 3 | 95% | 1.0 | −20 | 16 | 25 | 49 |
| 4 | 95% | 0.5 | +35 | 16 | 25 | 62 |
| 5 | 95% | 0.5 | −20 | 48 | 25 | 50 |
| 6 | 99% | 0.5 | −20 | 48 | 25 | 63 |
| 7 | 99% | 1.0 | −20 | 16 | 25 | 64 |
| 8 | 99% | 0.5 | +35 | 16 | 25 | 70 |
| 9 | 95% | 1.0 | +35 | 16 | 23 | 64 |
| 10 | 95% | 1.25 | +35 | 19 | 25 | 65 |
| 11 | 95% | 0.5 | +35 | 48 | 25 | 50 |
| 12 | 95% | 1.0 | +20 | 48 | 25 | 57 |
| 13 | 99% | 1.25 | +35 | 4 | 50 | 76 |
| 14 | 99% | 1.25 | +35 | 8 | 50 | 76 |
| 15 | 99% | 2.0 | +35 | 2 | 50 | 75 |
| 16 | 99% | 2.0 | +35 | 6 | 50 | 74 |
| 17 | 99% | 1.25 | +35 | 19 | 25 | 79[4] |
| 18 | 99% | 1.25 | +35 | 48 | 20 | 86[4] |

TABLE I-continued

| Reaction | Sulfuric Acid | Concentration L-Ascorbic Acid, M | Molar Excess of Lauric Acid, % | Reaction Period, Hr. | Temp., °C | Yield[1] |
|---|---|---|---|---|---|---|
| 19 | 99% | 1.25 | +35 | 42 | 25 | 77 |

[1]Calculated from weight of chromatographically pure, dry product and based on L-ascorbic acid.
[2]Reaction conditions identical to those used in Example 1 of U. S. Patent No. 2,350,435 of P. A. Wells and D. Swern.
[3]Determined to be 93% pure by comparison of the samples u.v. absorption (265 nm and pH 7.0) with that of an analytically pure sample of L-ascorbyl 6-laurate.
[4]Determined to be 96% pure by u.v. absorbance as described in footnote (3).

The data in Table I demonstrates that the preferred methods of the present invention give measurably enhanced yields of L-ascorbyl 6-laurate as opposed to the prior art process (Reaction No. 1). The effect of using the most preferred methods of the invention is demonstrated in runs 13-19 wherein the yields range from about 74 to 86%, and this represents a significant improvement over the prior art. In addition, Reaction Nos. 13-19 prove that use of 99% $H_2SO_4$ and a molar excess of lauric acid greatly increase yields, and that this improvement is not greatly affected by changes in reaction temperature or reaction times. In addition, comparison of the yields of Reaction No. 18 with that of No. 17 demonstrates that the yield of ester was improved using a combination of lower temperature (ca. 20° C.) and longer reaction time (36-48 hrs) as opposed to somewhat higher temperatures (25°-30° C.) for shorter reaction periods (15-20 hr). This result was surprising since prior investigators did not report any benefits using reaction temperatures below normal room temperature. The effect of certain of these features singly is also apparent from Table I; but in order to more clearly demonstrate this, Table I has been broken down into sub-tables separately directed to (a) the effects on yield of $H_2SO_4$ concentration, (b) amounts of fatty acid, (c) reaction times, and (d) the use of a molar excess of fatty acid coupled with a relatively high molar ratio of the sum of the fatty acid and ascorbic acid to $H_2SO_4$ (e.g., from about 0.1 to 0.3). This data is given below:

TABLE II

| | (a) Effect of increasing the $H_2SO_4$ concentration from 95 to 99% | | | | | | |
|---|---|---|---|---|---|---|---|
| Reaction | Sulfuric Acid | Concentration L-Ascorbic Acid, M | Molar Excess of Lauric Acid, % | Reaction Period, Hr. | Temp., °C | Yield | % Increase |
| 5 | 95% | 0.5 | −20 | 48 | 25 | 50 | — |
| 6 | 99% | 0.5 | −20 | 48 | 25 | 63 | 26% |
| 3 | 95% | 1.0 | −20 | 16 | 25 | 49 | — |
| 7 | 99% | 1.0 | −20 | 16 | 25 | 64 | 31% |
| 4 | 95% | 0.5 | +35 | 16 | 25 | 62 | — |
| 8 | 99% | 0.5 | +35 | 16 | 25 | 70 | 13% |

As can be seen from the foregoing, in each case the use of 99% $H_2SO_4$, as opposed to 95% $H_2SO_4$, leads to an increase in yield up to about 31%, based upon the respective controls in each instance. All other variables in the reactions are held constant between the sets of runs.

TABLE III

| | (b) Effect of increasing the amount of fatty acid | | | | | | |
|---|---|---|---|---|---|---|---|
| Reaction | Sulfuric Acid | Concentration L-Ascorbic Acid, M | Molar Excess of Lauric Acid, % | Reaction Period, Hr. | Temp., °C | Yield | % Increase |
| 3 | 95% | 1.0 | −20 | 16 | 25 | 49 | — |
| 9 | 95% | 1.0 | +35 | 16 | 25 | 64 | 31% |
| 2 | 99% | 0.5 | −20 | 16 | 25 | 50 | — |
| 8 | 99% | 0.5 | +35 | 16 | 25 | 70 | 40% |
| 5 | 95% | 0.5 | −20 | 48 | 25 | 50 | — |
| 11 | 95% | 0.5 | +35 | 48 | 25 | 50 | — |

Note that in the 16 hour reaction-time tests the yields were increased up to about 40%; in the case of the 48 hour test, the increased reaction time is shown to compensate for the difference in yields attributable to the excess fatty acid in the 16 hour tests.

As noted above, the fact that an excess of fatty acid can be used to successfully drive the esterification reaction is extremely surprising. That is, it has heretofore been thought that ascorbic acid is unstable in $H_2SO_4$, and accordingly an excess of the ascorbic acid reagent should be required.

TABLE IV

| | (c) Effect of reaction times | | | | | | |
|---|---|---|---|---|---|---|---|
| Reaction | Sulfuric Acid | Concentration L-Ascorbic Acid, M | Molar Excess of Lauric Acid, % | Reaction Period, Hr. | Temp., °C | Yield | % Increase |
| 2 | 99% | 0.5 | −20 | 16 | 25 | 50 | — |
| 6 | 99% | 0.5 | −20 | 48 | 25 | 63 | 26% |
| 15 | 99% | 2.0 | +35 | 2 | 50 | 75 | — |
| 16 | 99% | 2.0 | +35 | 6 | 50 | 74 | — |
| 17 | 99% | 1.25 | +35 | 19 | 25 | 79 | — |
| 19 | 99% | 1.25 | +35 | 42 | 25 | 77 | — |
| 13 | 99% | 1.25 | +35 | 4 | 50 | 76 | — |
| 14 | 99% | 1.25 | +35 | 8 | 50 | 76 | — |
| 3 | 95% | 1.0 | −20 | 16 | 25 | 49 | — |
| 12 | 95% | 1.0 | −20 | 48 | 25 | 57 | 16% |

The above results demonstrate that, especially using the preferred method of the invention (i.e., excess of lauric acid, 97% H₂SO₄), reaction times are not critical to good yield, and that these times can be widely varied, e.g., from about 2 to 48 hours. Thus, in accordance with the preferred form of the invention, significantly less reaction time is needed to produce the desired esters than has heretofore been required.

¹TABLE V (d) Effect of using a molar excess of fatty acid and a relatively high molar ratio of the sum of the fatty acid and ascorbic acid to $H_2SO_4$

| Reaction | Moles $H_2SO_4$ | ²Moles A.A. | ³Moles L.A. | Moles L.A. / Moles A.A. | Moles L.A. + Moles A.A. / Moles $H_2SO_4$ | Yield % |
|---|---|---|---|---|---|---|
| 1  | 1.870 | 0.050  | 0.040 | 0.80 | 0.048 | 54 |
| 2  | 0.937 | 0.025  | 0.020 | 0.80 | 0.048 | 50 |
| 3  | 0.937 | 0.050  | 0.040 | 0.80 | 0.096 | 49 |
| 4  | 0.937 | 0.025  | 0.034 | 1.35 | 0.063 | 62 |
| 5  | 0.937 | 0.025  | 0.020 | 0.80 | 0.048 | 50 |
| 6  | 0.937 | 0.025  | 0.020 | 0.80 | 0.048 | 63 |
| 7  | 0.937 | 0.050  | 0.040 | 0.80 | 0.096 | 64 |
| 8  | 0.937 | 0.025  | 0.034 | 1.35 | 0.063 | 70 |
| 9  | 0.937 | 0.050  | 0.060 | 1.35 | 0.126 | 64 |
| 10 | 0.937 | 0.0625 | 0.084 | 1.35 | 0.156 | 65 |
| 11 | 0.937 | 0.025  | 0.034 | 1.35 | 0.063 | 50 |
| 12 | 0.937 | 0.050  | 0.40  | 0.80 | 0.096 | 57 |
| 13 | 0.937 | 0.0625 | 0.084 | 1.35 | 0.156 | 76 |
| 14 | 0.937 | 0.0625 | 0.084 | 1.35 | 0.156 | 76 |
| 15 | 0.937 | 0.100  | 0.135 | 1.35 | 0.251 | 75 |
| 16 | 0.937 | 0.100  | 0.135 | 1.35 | 0.251 | 74 |
| 17 | 0.937 | 0.0625 | 0.084 | 1.35 | 0.156 | 79 |
| 18 | 0.937 | 0.0625 | 0.084 | 1.35 | 0.156 | 86 |
| 19 | 0.937 | 0.0625 | 0.084 | 1.35 | 0.156 | 77 |

¹In this table the molar quantities specified have been calculated from Table I, using density of 1833.7 g/l for 95% $H_2SO_4$ and 1834.2 g/l for 99% $H_2SO_4$.
²Moles of Ascorbic Acid
³Moles of Lauric Acid It is of especial interest that only reaction Nos. 9, 10, 13-19 meet the dual requirements of using an excess of fatty acid relative to the ascorbic acid, and a relatively high molar ratio of the sum of lauric and ascorbic acid to $H_2SO_4$ of from about 0.1 to 0.3. Surprisingly, all of these runs also have excellent yields relative to the remainder of the runs; however, the lower yields with Runs 9 and 10 relative to Runs 13-19 are believed to stem from the use of 95% $H_2SO_4$ as opposed to 99% $H_2SO_4$ in the latter series of runs. In any event, the effect of the defined molar ratio on ester yields is conclusively demonstrated.

EXAMPLE II

In this test a quantity of D-isoascobic acid was used instead of the L-ascorbic acid used in the previous reactions, in order to demonstrate that the methods hereof are applicable to other isomers of ascorbic acid.

In particular, a solution of D-isoascorbic acid (0.05 moles) in 99% sulfuric acid (50 ml, 0.937 moles) at room temperature was prepared and palmitic acid (0.0675 moles) was added thereto. The mixture was stirred, at 25° for 40 hrs., and D-isoascorbyl 6-palmitate (16.02 g, 77.5%) was isolated as previously described. The crude crystals of D-isoascorbyl 6-palmitate was recrystallized from a mixture of ether-petroleum ether to give pure material with m.p. 87-88.5°. Swern et al., Oil and Soap, 20 (1943) 224 reported the compound had m.p. 88.5°-89.5°. In a control experiment using 95% $H_2SO_4$ and the esterification conditions described in Example 1 of U.S. Pat. No. 2,350,435, the yield of D-isoascorbyl 6-palmitate was 38%.

Note that the mole ratio of the sum of palmitic acid and D-isoascorbic acid to sulfuric acid is 0.125, in accordance with the preferred embodiment of the invention.

EXAMPLE III

The structure of L-ascorbyl 6-palmitate produced in accordance with the present invention was confirmed by elemental analysis and carbon-13 resonance spectroscopy. A monopalmitate ester of L-ascorbic acid has the elemental composition $C_{22}H_{38}O_7$, which requires 63.74% carbon and 9.25% hydrogen. The experimental analysis gave 63.44% carbon and 9.21% hydrogen. The carbon-13 spectra were measured in dimethyl sulfoxide solution at a frequency of 25.15 MHz by the pulse Fourier-Transform method using a Varian XL-100-15 spectrometer and a Nicolet computer system. Deuterium oxide was placed in a coaxial sample tube inside the main sample tube containing the dimethyl sulfoxide solution of a L-ascorbyl compound. Deuterium oxide was used as a field frequency lock, and the chemical shifts of carbons were calculated with reference to tetramethylsilane (TMS) using the principal $^{13}C$-signal of dimethyl sulfoxide at 40.50 p.p.m. downfield from TMS.

The signals of the carbon atoms in L-ascorbic acid (see Table VI) were assigned as follows. The lactone carbon (carbon 1) was assigned to the signal furthest downfield (170.9 p.p.m.), since this signal lies in the general range of 157-180 p.p.m. typical of ester carbonyl carbons (G. D. Levy and G. L. Nelson, "Carbon-13 Nuclear Magnetic Resonance for Organic Chemists," Wiley-Interscience, New York, NY (1972) p. 109). The assignment of C-3 to the signal at 153.2 p.p.m. was deduced from the known shifts of alkene carbons (generally 80-145 p.p.m.), and from the fact that the C-3 carbon of L-ascorbic would be expected to be shifted to somewhat lower field than normally found for alkene signals since carbon-3 is attached to the ionizing 3-OH. It is known that ionization of carboxylic acids shifts the signal of a carboxyl carbon by approximately 5 p.p.m. downfield relative to that of the undissociated carboxyl carbon (Levy and Nelson, ibid., p. 116). X-ray crystallography has shown the 3-OH of L-ascorbic acid is the acidic group, and therefore the signal of C-3 would be to lower field than that of the 2-carbon of L-ascorbic acid. The C-2 carbon was therefore assigned to the other enolic carbon signal at 118.3 p.p.m.

The C-4 signal was determined by converting L-ascorbic acid to 4-deuterio-L-ascorbic acid (G. S. Brenner, D. F. Hinkley, L. M. Perkins, and S. Weber, J. Org. Chem., 29 (1964) 2389; and E. M. Bell E. M. Baker, and B. M. Tolbert, J. Labeled Compds. 2(2) (1966) 148). The $^1$H-decoupled spectrum of the 4-deuterio compound showed a weak triplet centered at 75.0 p.p.m., which is expected for the deuterated methine carbon.

TABLE VI

| | [1]Chemical Shifts in Methyl Sulfoxide | |
|---|---|---|
| Carbon | L-Ascorbic Acid | L-Ascorbyl 6-palmitate |
| 1 | 170.9 | 170.2 |
| 2 | 118.3 | 118.2 |
| 3 | 153.2 | 152.1 |
| 4 | 75.0 | 75.1 |
| 5 | 68.8 | 65.7 |
| 6 | 62.4 | 64.5 |

[1]Chemical shifts in p.p.m. from external standard of tetramethylsilane.

The C-6 signal was assigned to the resonance at 62.4, p.p.m., which is characteristic of the C-6 methylol carbons in hexose sugars (A. S. Perlin, B. Casu, and H. J. Koch, Can. J. Chem., 48 (1970) 2596). The signal at 62.4 p.p.m. also gave a triplet in off-resonance decoupling experiments, confirming that the signal was from a methylene carbon. The remaining signal, (68.8 p.p.m.) in the spectrum of L-ascorbic acid, gave a doublet in off-resonance decoupling experiments, and was assigned to C-5.

The structure of L-ascorbyl 6-palmitate, which was assigned to the product isolated from the esterification reaction, was in full accord with its $^{13}$C-n.m.r. spectrum. As expected from model compound studies (Levy and Nelson, ibid., p. 47), esterification at the C-6 position of L-ascorbic acid shifted the signal of C-6 downfield by 2.1 p.p.m. whereas the signal of C-5 was shifted upfield by 3.1 p.p.m. The other signals of the carbons in the ester were very similar, as expected, to those of L-ascorbic acid.

The $^{13}$C spectrum of L-ascorbyl 6-palmitate also showed the fatty acid carbonyl carbon at 172.5 p.p.m. as well as eight other resolved signals assigned to the aliphatic carbons of the fatty acid residue.

EXAMPLE IV

Solutions of 95%, 96%, 97%, and 98% sulfuric acid were prepared by adding, respectively, 1.93 ml., 1.43 ml., 0.95 ml., and 0.47 ml of distilled water to 23.1 ml., 23.6 ml., 24.1 ml., and 24.5 ml. of 99% (37±0.15N; Fisher Scientific, Fairlawn, N. J.) sulfuric acid. 6.01 g (30 mmol) of lauric acid and 4.40 g (25 mmol) of L-ascorbic acid were added to 25 ml of each sulfuric acid medium. The solutions were stirred at 26° for ca. 1 hr. and allowed to stand at ca. 26° for 19 hr. Each solution was then poured into 400 ml. of crushed ice with vigorous stirring and extracted with one 500 ml. and one 100 ml. portion of ether. Small quantities of ammonium sulfate were used to help break emulsions. The solutions were dried over sodium sulfate, then magnesium sulfate, filtered, and evaporated to dryness on a rotary vacuum evaporator. Each product was thoroughly washed with 600 ml., 500 ml., and 300 ml. portions of petroleum ether and vacuum dried to give the following yields:

TABLE VII

| % Sulfuric Acid | 95 | 96 | 97 | [1]98 | 99 |
|---|---|---|---|---|---|
| Yield (g) | 5.84 | 6.58 | 6.61 | — | 7.09 |

TABLE VII-continued

| % Sulfuric Acid | 95 | 96 | 97 | [1]98 | 99 |
|---|---|---|---|---|---|
| Yield (%) | 65.2 | 73.3 | 73.8 | — | 79.0 |

[1]Samples lost

The 98% sulfuric acid was prepared as before, whereas 100% sulfuric acid was prepared either by adding 4.3 ml of 20-23% fuming sulfuric acid to 20.7 ml of 99% sulfuric acid or by the "fair and foggy" procedure of Kunzler, Anal. Chem., 25 (1953) 93. In addition, 4-5% fuming sulfuric acid was prepared by mixing 10.0 ml (18.97 g) of 20-23% fuming sulfuric acid with 39.2 ml (71.8 g) of 100% sulfuric acid. The identical reaction as set forth above with these acid formulations gave the following results:

TABLE VIII

| % Sulfuric Acid | 98 | 99 | 100 | 4-5% fuming |
|---|---|---|---|---|
| Yield (g) | 6.95 | 6.94 | 6.73 | 6.43 |
| Yield (%) | 77.6 | 77.5 | 75.1 | 65.0 |

Tables VII and VIII above further demonstrate the fact that the yield of ester is highly dependent on the initial water content in the sulfuric acid medium; highly concentrated sulfuric acid is the most useful in the esterification method hereof. In this connection, the data of Table VII demonstrate that simply going from 95% to 96% $H_2SO_4$ gives a statistically significant increase in yields and that this effect is maintained at the higher concentration levels.

EXAMPLE V

The appropriate concentrations of sulfuric acid were prepared as shown in the table below. To each of 5 mixtures of 3.52 g (20 mmol) of L-ascorbic acid and 6.98 g (27.2 mmol) of palmitic acid was added 20 ml. of one of the prepared sulfuric acid solutions with stirring at 20° C. for 25 min., and periodic stirring at 20° until all the solid was dissolved. The solutions were kept at 20° for 36 hr. and worked up in the usual manner to give the yields shown after petroleum ether wash and vacuum drying.

TABLE IX

| $H_2SO_4$ (g) | $H_2O$ (g) | % $H_2SO_4$ | Yield (g) | Yield (%) |
|---|---|---|---|---|
| 46.82 | .702 | 98.52 | 6.55 | 79.0 |
| 45.30 | .566 | 98.77 | 6.79 | 81.9 |
| 47.65 | .477 | 99.01 | 6.80 | 82.0 |
| 49.10 | .368 | 99.26 | 7.08 | 85.4 |
| 46.98 | .235 | 99.50 | 7.05 | 85.0 |

The above data further demonstrates the beneficial effect on ester yield of highly concentrated $H_2SO_4$, and the use of relatively low (20° C.) reaction temperatures for long reaction times.

Having thus described the invention, what is claimed as new and desired to be secured by Letters Patent is:

1. A process of preparing fatty acid esters of ascorbic acid, comprising the steps of:
    preparing a homogeneous mixture comprising respective quantities of (1) a member selected from the group consisting of the isomers of ascorbic acid, (2) sulfuric acid having a concentration of from about 95 to 100%, and (3) a saturated fatty acid having from 12 to 18 carbon atoms, inclusive,
    said fatty acid being present in a molar excess relative to said member, the molar ratio of the sum of said fatty acid and member to said concentrated sulfuric acid being from about 0.1 to 0.3 allowing said mixture to react to form an ester of said fatty acid; and recovering said fatty acid ester.

2. The method as set forth in claim 1 wherein said sulfuric acid has a concentration of from about 98 to 99%.

3. The method as set forth in claim 1 wherein said member is L-ascorbic acid.

4. The method as set forth in claim 1 wherein said mixture is maintained at a temperature of from about 20 to 50° C. during said formation of the fatty acid ester.

5. The method as set forth in claim 1 wherein said temperature is about 20° to 25° C.

6. The method as set forth in claim 1 wherein said ester-forming reaction is allowed to run for a period of from 2 to 48 hours.

7. The method as set forth in claim 1 wherein said period is from 4 to 16 hours.

8. A process of preparing fatty acid esters of ascorbic acid, comprising the steps of:

preparing a homogeneous mixture comprising respective quantities of (1) a member selected from the group consisting of the isomers of ascorbic acid, (2) sulfuric acid having a concentration of from about 95 to 100%, and (3) a saturated fatty acid having from 12 to 18 carbon atoms, inclusive, said fatty acid being present in a molar excess relative to said member, the mole ratio of the sum of fatty acid and member to said concentrated sulfuric acid being from about 0.1 to 0.3;

allowing said mixture to react for a period of from 2 to 48 hours and at a temperature of from 20° to 50° C. to form an ester of said fatty acid; and recovering said fatty acid ester.

* * * * *